United States Patent
Hanni et al.

(10) Patent No.: US 6,756,495 B1
(45) Date of Patent: Jun. 29, 2004

(54) METHOD FOR DETECTING THE PRESENCE OF BIOLOGICAL MATTERS OF BOVINE ORIGIN, AND OLIGONUCLEOTIDES FOR ITS IMPLEMENTATION

(75) Inventors: Catherine Hanni, Lyons (FR); Vincent Laudet, Lyons (FR); Corine Grangette, Anstaing (FR); Marc Lange, Euralille (FR); Stephane Pasteau, Lamnersart (FR)

(73) Assignee: Centre National de la Recherche Scientifique, Paris Cedex (FR)

( * ) Notice: Subject to any disclaimer, the term of this patent is extended or adjusted under 35 U.S.C. 154(b) by 0 days.

(21) Appl. No.: 09/423,259

(22) PCT Filed: May 4, 1998

(86) PCT No.: PCT/FR98/00892

§ 371 (c)(1),
(2), (4) Date: Mar. 2, 2000

(87) PCT Pub. No.: WO98/50401

PCT Pub. Date: Nov. 12, 1998

(30) Foreign Application Priority Data

May 5, 1997 (FR) .......................................... 97 05517

(51) Int. Cl.[7] .............................................. C07H 21/04
(52) U.S. Cl. ....................... 536/24.33; 536/24.3; 435/6; 435/91.2
(58) Field of Search ............................ 536/24.31, 24.3, 536/23.1; 435/6, 91.2

(56) References Cited

U.S. PATENT DOCUMENTS 5,596,089 A * 1/1997 Silversides et al. ........ 536/24.3

FOREIGN PATENT DOCUMENTS

| EP | 0 464 010 | 1/1992 |
| EP | 0 546 762 | 6/1993 |
| WO | WO 94/14968 | 7/1994 |
| WO | WO 94/28177 | 12/1994 |

OTHER PUBLICATIONS

Loftus et al. PNAS USA vol. 91, pp. 2737–2761, Mar. 1994.*
Fei et al. Animal Science and Technology (1996) vol. 67, No. 10, pp. 900–905.*
M. C. Sinclair et al., "PCR Strategies for Isolation of the 5' End of an Immunoglobulin–encoding Bovine cDNA", *Gene*, vol. 1, No. 167, 1995, Elsevier Science B.V., pp. 285–289.

* cited by examiner

*Primary Examiner*—Jeffrey Fredman
*Assistant Examiner*—Juliet C. Switzer
(74) *Attorney, Agent, or Firm*—Young & Thompson

(57) ABSTRACT

The present invention is a process for obtaining a fragment of bovine DNA which has a defined size and is specific to bovines, and in particular the species *Bos taurus* and *Bos indicus*, from a sample of organic matter, and a process by which a defined sequence of the bovine genome present in bovine genomes but absent from the genomes of other animal species is amplified by a polymerase chain reaction.

2 Claims, 2 Drawing Sheets

METHOD FOR DETECTING THE PRESENCE OF BIOLOGICAL MATTERS OF BOVINE ORIGIN, AND OLIGONUCLEOTIDES FOR ITS IMPLEMENTATION

The present invention relates to a process for detection of the presence of biological matters of bovine origin in a sample of organic matter.

It also relates to oligonucleotides for carrying out this process.

In 1986, bovine spongiform encephalopathy (BSE), or "mad cow" disease, showed up for the first time in British bovine livestock. Since then, more than 100,000 clinical cases have been identified in cattle. This disease, which is present in Great Britain, has as endemic evolution. It has also been observed in various European countries: Ireland, Switzerland, France, Denmark, Germany—where it evolves sporadically.

The clinical picture of the disease is known. The infectious agent responsible, called "prion" is characterized by, among other properties, an extreme resistance to conventional decontaminating agents, such as heat, radiation or detergents. Recent studies furthermore have demonstrated the very high resistance of the infectious agent under "natural" conditions, and in particular its persistence in pastures. The infectiousness can therefore persist in the ground for at least 3 years.

One of the modes of transmission of the infectious agent is ingestion of contaminated foods, and this transmission can furthermore be from one animal species to another.

Analysis of the epidemiological data has enabled the origin of the English epidemic to be discovered, this being due to the infectious agent contaminating the meat meals and bone meals (MBM) used to manufacture food additives intended for feeding dairy cows. These meals are the by-products of quartering shops arising from treatment of carcasses and waste originating from abattoirs.

The structures of "prion" is not known to this day, and there is no test for detecting it.

It therefore important to determine whether organic matter contains biological matters of bovine origin and is capable of containing "prions".

In the agricultural food field, the characterization of animal species initially used biochemical techniques for analysis of proteins (BARA et al. 1992, Trends in Food Science and Technology, 3, 69–72; SOTELO et al. 1993, Trends in Food Science and Technology, 4, 395–401; Hernandez et al., Food and Agricultural Immunology, 6, 95–104). However, these methods are not very specific (electrophoresis), or are incompatible with denaturation of the samples to be analysed (immunoanalysis). They are now progressively being replaced by the techniques of DNA analysis, this molecule being less sensitive than proteins to denaturing physico-chemical conditions.

Identification of the main animal species of interest was first carried out by the technique of hybridization of nucleic probes (BUNTJER et al. 1995, Zeitschrift fuer Lebensmittel Untersuchung und Forschung 201 (6): 577–582; MEYER et al., 1994, Fleischwirtschaft 74 (11) 1237–1238; TSUMURA et al. 1992, Journal of Japanese Society of Food Science and Technology 39 (1) 60–63; EBBEHOJ and THOMSEN, 1991, Meat Science 30 (4): 359–366; BAUER et al., 1987, Archiv fuer Lebensmittelhygiene 38 (6): 172–174; EBBEHOJ and THOMSEN, 1991, Meat Science 30 (3): 221–234).

This technology, which is tricky to use, has now been superseded by the PCR (polymerase chain reaction) method, which has been used to characterize biological matters originating from various animal species.

The only methods for amplification by PCR described in beef (Bos taurus) use amplification of the mitochondrial DNA (mtDNA) region which codes for a cytochrome by means of PCR primers which recognize sequences conserved in species of vertebrates, and then their characterization by means of restriction enzymes (RFLP) or by sequencing (MEYER et al. 1995, Journal of AOAC—International 78 (6): 1542–1551; CHIKUNI et al. 1994, Animal Science and Technology, 65 (6): 571–579; GUGLICH at al. 1994, J. Forensic. Sci. 39 (2): 353–61).

The organization and complete sequence of bovine mitochondrial DNA (mtDNA) are known (ANDERSON et al. 1982, J. Mol. Biol. 156 (4): 683–717). On the basis of these data, several works have been dedicated to the study of the genetic variability of the mitochondrial genome of domestic Bovidae by analysis of the restriction polymorphism (CHEN et al. 1995, Comp. Biochem. Physiol. B. Biochem. Mol. Biol. 111 (4): 643–649; KIKKAWA et al. 1995, Biochem. Genet. 33; (1–2): 51–60; BRADLEY et al. 1994, Anim. Genet (4): 265–271; AMANO et al. 1994, Anim. Genet. 25 (1): 29–36; SUZUKI et al. 1993, Anim. Genet 24 (5): 339–343: Lan et al. 1993, I. Chuan. Hsueh Pao 20 (5): 419–425; BHAT et al. 1990, Biochem. Genet 28 (7–8): 311–318; LOFTUS et al., 1994, Anim. Genet. 25:265–271) or by sequencing (LOFTUS et al. 1994, Proc. Natl. Sci. USA 91 (7): 2757–2761; RON et al. 1993, Anim. Genet. 24 (3): 183–186; BRADLEY et al., 1996, Proc. Natl. Acad. Sci. USA 93: 5131–5135; BAILEY et al., 1996, Proc. R Soc. Lond. B, 263:1467–1473).

Partial sequencing of the control region of bovine mtDNA has furthermore been carried out for various European, African and Indian bovine breeds (LOFTUS et al., 1994 Proc. Natl. Sci. USA 91 (7): 2757–2761; BRADLEY et al., 1996, Proc. Natl. Acad. Sci. USA 93: 5131–5135; BAILEY et al., 1996, Proc. R. Soc. Lond. B, 263:1467–1473).

It thus emerges from studying the prior art that works on analyses of the DNA of certain species and bovine breeds have already been carried out. Nevertheless, none of the documents of the prior art describes a specific and sensitive method for amplification of bovine DNA which enables traces of biological matters of bovine origin to be identified and can be used for all bovine breeds and in organic matter having widely varying compositions.

In fact, the known techniques for identification of bovine DNA (for example analysis of genomes by RFLP or PCR-RFLP carried out on portions of sequences which vary little) have disadvantages. By these methods, which are not very specific, it is often difficult to analyse mixtures of DNA originating from different species because of the large number of bands and the difficulties in interpretation associated with this characteristic.

The low sensitivity of some of these techniques does not enable the presence of organic matter of bovine origin in widely diverse organic substrates to be demonstrated in a reliable manner. These methods cannot be used if the DNA present in the sample is degraded in the form of small fragments having a size of less than about 500 base pairs.

The problem of identification of organic matter originating from any of the bovine breed is particularly crucial, since bovine spongiform encephalitis is not limited to European bovine breeds, but extends to African and Indian breeds (Bos taurus and Bos indicus).

The Applicant has thus concerned himself with solving these problems.

It has been found that the presence of biological matter of bovine origin could be detected in a specific and simple manner and with a high sensitivity, whatever the bovine breed (*Bos taurus* and *Bos indicus*), in samples of organic matter by amplifying a defined sequence of the bovine genome in a specific manner.

In its most general form, the present invention thus relates to a process for obtaining a fragment of bovine DNA which has a defined size and sequence and is specific to bovines, and in particular the species *Bos taurus* and *Bos indicus*, from a sample of organic matter, and a process by which a defined sequence of the bovine genome present in bovine genomes but absent from the genomes of other animal species is amplified by a polymerase chain reaction.

The present invention also relates to a process for detection and identification of the presence of biological matter of bovine origin in a sample of organic matter, characterized in that the presence of DNA of bovine origin is determined in the said organic matter by amplification of a specific DNA sequence of the bovine genome.

Organic matter is understood as meaning any solid or liquid matter which is assumed to have at least partly a biological origin.

The DNA sequence is advantageously of mitochondrial origin. The choice of a mitochondrial sequence is particularly advantageous, since in an animal cell there are about 100 to 1,000 copies of mitochondrial DNA for one copy of nuclear DNA. In the event of degradation of the DNA, the probability of detecting the mitochondrial DNA is thus much higher than the probability of detecting the nuclear DNA. In addition, the mitochondrial DNA is more resistant to degradation than the nuclear DNA. The mitochondrial DNA can therefore be detected more reliably in organic matter in which the DNA is subjected to various physical factors (heat, pressure . . . ), chemical factors (hydrolysis, oxidation . . . ) or biochemical factors which tend to degrade it.

This characteristic proves to be particularly important if the intention is to detect the presence of biological matter of bovine origin in organic matter which has been subjected to several transformations, for example in cosmetics, in agricultural foods, such as the meals used for feeding cattle, composts, manures and dungs etc. . . .

The invention is also advantageous for detection of the presence of biological matters of bovine origin in the following organic substrates: raw, smoked or cooked meats, pellets, blood and products based on blood, milk and products based on milk, bone and products based on bone, hides, skins, ivories, furs, horns and products based on horn, guano, faeces, semi-liquid manures, liquid manures, gelatine and products based on gelatine, and cosmetic and agricultural food products.

The invention relates to specific mitochondrial DNA fragments of the bovine genome having sizes ranging from about 500 base pairs to about 100 base pairs, in particular about 152 to 480 base pairs, and having a sequence identical to the extent of at least 80%, and preferably to the extent of at least 90%, to homologous regions of the sequence of the control region of the mitochondrial DNA determined by ANDERSON et al., 1982, J. Mol. Biol., 156, 683–717 and in particular ranging from position 15,824 to position 171, these positions being determined according to the complete mitochondrial DNA sequence of beef, which comprises 16,338 nucleotides, determined by ANDERSON et al., 1982, J. Mol. Biol., 156, 683–717.

Preferably, the DNA amplification is carried out by the polymerase chain amplification method (PCR), comprising repetition of a cycle made up of the following stages:

Heating of the DNA extracted from the sample of organic matter such that the DNA is separated into two monocatenated stands.

Hybridization of oligonucleotide primers with the monocatenated DNA strands at an appropriate temperature and Elongation, of the oligonucleotide primers by a polymerase at an appropriate temperature.

Particularly preferably, one of the primers is an oligonucleotide having a sequence identical to the extent of at least 80%, preferably to the extent of at least 90%, and advantageously to the extent of at least 95%, to an oligonucleotide made up of a sequence of about 15 to 25 nucleotides, in particular about 20 to 25 nucleotides, contained in the following sequence SEQ ID No. 1 (positions 136 to 178 according to ANDERSON et al., 1982, J. Mol. Biol., 156, 683–717):

TAATGTCCATGCTTATCATTATGCTGGT-GCTCAAGATGCAGTT

This first primer can be, in particular, an oligonucleotide or a mixture of oligonucleotides comprising the following sequence SEQ ID No. 2 (positions 152 to 166 according to ANDERSON et al., 1982, J. Mol. Biol., 156, 683–717):

YTATCATTATGCTGG in which Y is T or C.

It is preferably an oligonucleotide or a mixture of oligonucleotides having the following sequence SEQ ID No. 3 (positions 152 to 171 according to ANDERSON et al., 1982, J. Mol. Biol., 156, 683–717):

CATGCYTATCATTATGCTGG PBR6)

in which Y is T or C.

The second primer is an oligonucleotide having a sequence identical to the extent of at least 80%, preferably to the extent of at least 90%, and advantageously to the extent of at least 95%, to an oligonucleotide made up of a sequence of about 15 to 25 nucleotides, in particular about 20 to 25 nucleotides, contained in the following sequence SEQ ID No. 4 (positions 16,015 to 16,060 according to ANDERSON et al., 1982, J. Mol. Biol., 156, 683–717):

ATTATATGCCCCATGCATATAAGCAAG-TACATGACCTCTATAGCAG

Such an oligonucleotide is preferably that comprising the following sequence SEQ ID No. 5 (positions 16,034 to 16,048 according to ANDERSON et al., 1982, J. Mol. Biol., 156, 683–717):

TAAGCAAGTACATGA or preferably that having the following sequence SEQ ID No. 6 (positions 16,029 to 16,048 according to ANDERSON et al., 1982, J. Mol. Biol., 156, 683–717):

GCATATAAGCAAGTACATGA (PBF9)

Each of the oligonucleotides SEQ ID No. 1 to 3 is used as a pair with one or other of oligonucleotides SEQ ID No. 4 to 6. The most advantageous pair of primers is the pair SEQ ID No. 3 and SEQ ID No. 6.

According to a particularly advantageous embodiment of the present invention, at least part of the hybridization stages of the cycles which make up the amplification reaction is carried out at a temperature of about 50° C. to 58° C., in particular 50° C. to 55° C. In add the Applicant has found that a temperature of about 51° C. was particularly suitable for obtaining a specific amplification.

Such an embodiment enables a high amplification specificity to be obtained.

The temperatures of the stages of separation of the strands and elongation are advantageously about 94° C. and 72° C. respectively.

The process described above is specific since it gives no amplification reaction which can be detected in the presence of DNA of other than bovine origin (*Bos taurus* and *Bos indicus*). The use of the primers SEQ ID No. 1 to SEQ ID No. 6 gives rise only to a DNA fragment of about 480 base pairs. The present invention also relates to this oligonucleotide fragment.

It advantageously has a sequence identical to the extent of at least 80%, preferably 90%, and advantageously 95%, to the following sequence SEQ ID No. 8 (positions 16,029 to 171 according to the sequence of ANDERSON et al., 1982, J. Mol. Biol., 156, 683–717, which comprises 16,338 nucleotides):

GCATATAAGCAAGYACATRAYYYCTAYAVYAGTA
CATAAYRCATAYAATTATTRAYYGTACATAG
TACATTATRTCAAAYYCATYCTYRAYARYA
TATYTAYYATATAYYYCYTNCCAYTAGATCA
CGAGCTTAAYTACCATGCCGCGTGAAACCAR
CAACCCGCTRRGCAGNGGATCCCTCTTCT
CGCTCCGGGCCCATARAYYGTGGGGGTCGCTA
TYYARTGAAYTTTAYCAGGCATCTGGTTC
TTTCTTCAGGGCCATCTCATCTAAARYGT
CCATTCYTTCCTCTTAAATAAGACATCTCGATG
GACTAATGRCTAATCAGCCCATGCTCACACATA
ACTGTGYTGTCATACATTTGGTATTTTTA
TTTTGGGGGATGCTTGGACTCAGCTATGGC
CGTCAAAGGCCCTGACCCGGAGCATCTATTG
TAGCTGGACTTAACTGCATCTTGAGCACC
AGCATAATGATARGCRTG

R: A or G; Y: C or T; N: A, G, C or T

In this respect it can be seen that the Applicant has solved a certain number of technical problems for carrying out this process. Firstly, the choice of primers was a real problem, since it was necessary to select sequences which on the one hand are common to various bovine breeds and on the other hand hybridize in a stable manner under the very varied physico-chemical conditions representative of the wide diversity of organic matter which may contain biological matter of bovine origin.

The Applicant has also developed other oligonucleotide primers which are shown below and which have the characteristic of being able to generate smaller amplification fragments of a size less than about 200 base pairs and greater than 100 base pairs, and advantageously about 150 base pairs. The sequences of the oligonucleotide primers are the following:

SEQ ID No9: GAGCCTTATCAGTATTAAATTTATC (15824–15848)

SEQ ID No10: CATTAATGTTATGTACATTA (15962–15981)

SEQ ID No11: TTTCACGCGGCATGGTAATT (16162–16181)

SEQ ID No12: ATCCAATGAATTTTACCAGG (16245–16264)

SEQ ID No13: GTCAATGGTCACAGGACATA (181–200)

SEQ ID No14: ATTGACTTTGTTTGGAGTGC (319–338)

The positions of these nucleotide primers defined according to the sequence of ANDERSON et al., 1982, J. Mol. Biol., 156, 683–717 are indicated in parenthesis.

The invention also relates to pairs of oligonucleotide primers, characterized in that the oligonucleotides of which they consist are chosen from those:

having a sequence identical to the extent of at least 80%, preferably 90%, and advantageously 95%, to an oligonucleotide made up of a sequence of about 15 to 25 nucleotides, in particular 20 to 25 nucleotides, comprising at least 10 contiguous nucleotides of the following SEQ ID No. 9:

GAGCCTTATCAGTATTAAATTTATC or of the following sequence ID No. 10:
CATTAATGTTATGTACATTA or of the following sequence SEQ ID No. 11:
TTTCACGCGGCATGGTAATT or of the following sequence SEQ ID No. 12:
ATCCAATGAATTTTACCAGG or of the following sequence SEQ ID No. 13:
GTCAATGGTCACAGGACATA or of the following sequence SEQ ID No. 14:
ATTGACTTTGTTTGGAGTGC Each of the oligonucleotide primers SEQ ID No. 4 to 6 and SEQ ID No. 9, 12 and 13 is used as a pair with one or other of the oligonucleotide primers SEQ ID No. 1 to 3 and SEQ ID No. 10, 11 and 14. The most advantageous pairs of oligonucleotide primers are the following: SEQ ID No. 9 with SEQ ID No. 10, SEQ ID No. 6 with SEQ ID No. 11, SEQ ID No. 12 with SEQ ID No. 3, SEQ ID No. 13 with SEQ ID No. 14.

The pair of primers SEQ ID No. 9 with SEQ ID No. 10 enables the fragment advantageously having a sequence identical to the extent of at least 80%, preferably 90%, and advantageously 95%, to the following DNA fragment to be obtained:

SEQ ID No15 (positions 15824–15981): GAGCCTTATC
AGTATTAAATTTATCAAAAATCCCAATAACTCA
ACACAGAATTTGCACCCTAACCAAATATTAC
AAACAC CACTAGCTAACATAACACGCCCATAC
ACAGACCACAGAATGAATTACCTACGCA
AGGGGTAATGTACATAACATTAATG The pair of primers SEQ ID No. 6 with SEQ ID No. 11 enables the fragment advantageously having a sequence identical to the extent of at least 80%, preferably 90%, and advantageously 95%, to the following DNA fragment to be obtained:

SEQ ID No16 (positions 16029–16181): GCATATAAGC
AAGTACATGACCTCTATAGCAGTACATAAT
ACATATAATTATTGACTGTACATAGTACATTAT
GTCAAATTCATTCTTGATAGTATATCTATTATA
TATTCCTTACCATTAGATCACGAGMTAATRACC
ATGCCGCGTGAAA The pair of primers SEQ ID No. 12 with SEQ ID No. 3 enables the fragment advantageously having a sequence identical to the extent of at least 80%, preferably 90%, and advantageously 95%, to the following DNA fragment to be obtained:

SEQ ID No17 (positions 16245–171): ATCCAATG
AATTTTACCAGGCATCTGGTTCTTTCAGGGCC
ATCTCATCTAAAACGGTCCATTCTTTCCT
CTTAAATAAGACATCTCGATGGACTAATGGC
TAATCAGCCCATGCTCACACATAACTGTGC
TGTCATACATTTGGTATTTTTTATTTTGGGGGA
TGCTTGGACTCAGCTATGGCCGTCAAAGGCC
CTGACCCGGAGCATCTATTGTAGCTGGACTTAA
CTGCATCTTGAGCACCAGCATAATGATA
AGCATG The pair of primers SEQ ID No. 13 with SEQ ID No. 14 enables the fragment advantageously having a sequence identical to the extent of at least 80%, preferably 90%, and advantageously 95%, to the following DNA fragment to be obtained:

SEQ ID No18 positions 181–338): GTCAATGGTCACA GGACATAAATTATATTATATATCCCCCCTTCATAA AAATTCCCCCCTTAAATATCTACCACCACTT TTAACAGACTTTTCCCTAGATACTTATTTAAATT TTTCACGCAACAATACTCAATTTAGCACTC CAAACAAAGTCAAT The amplification products described above, and in particular the sequences SEQ ID No. 15 to SEQ ID No. 18, can be detected if a significant fraction of the DNA is degraded, that is to say after the action of the physical, chemical and/or biochemical factors described above and during transformations of organic substrates.

The experimenter preferably searches for the presence of SEQ ID No. 8, described above, with the aid of suitable primers, and in the case where the detection is negative, searches for the fragments of lower size, and in particular those of about 150 to 260 base pairs generated, in particular, by the use of the primers SEQ ID No. 9 to SEQ ID No. 14.

The use of primers SEQ ID No. 9 to SEQ ID No. 14 gives rise only to single DNA fragments of about 150 to 260 base pairs. The process described above is specific since it gives no amplification reaction which can be detected in the presence of DNA of other than bovine origin. The present, invention also relates to these oligonucleotide fragments.

The uniqueness of the amplification product is another advantage of the present invention, enabling a high sensitivity to be obtained and greatly facilitating interpretation of the results.

The process according to the present invention thus has a large number of advantages with respect to the techniques of identification of bovine DNA which are already known.

The process described thus has a high simplicity in its interpretation because of the production of a single and unique product which is specific to bovine DNA and which thus is not found in products of amplification of DNA of other species.

Reading of the migration profiles of the amplification products obtained with the process according to the present invention thus comprises simply determination of the presence of a single and unique migration band in an electrophoresis gel. In the absence of such a band, it can be considered that there are no detectable traces of bovine DNA. In contrast, the presence of a band indicates that bovine DNA is present in the sample, and thus that the sample in question contains biological matter of bovine origin.

The amplification product can be demonstrated by any method known to those skilled in the art, and in particular by simple electrophoresis on an agarose gel. This amplification product can be sequenced in order to determine the nucleotide sequence and to confirm its identity. It can also be demonstrated by hybridization with a probe comprising an oligonucleotide part and a marker. The oligonucleotide which make up this probe comprises a minimum of about 15 nucleotides, preferably a minimum of about 20 nucleotides.

To confirm the identity of the fragment SEQ ID No. 8, an oligonucleotide in which part of the sequence is identical to the extent of at least 80%, preferably 90%, to the following sequences SEQ ID No. 7 or No. 19 is used:

SEQ ID No7 (16114–16140): CTTGATAGTATATCTAT-TATATATTCC (BH1)

SEQ ID No19 (16227–16251): TAARC-CGTGGGGGTCGCTATCCAAT (BH2)

where R is G or A;

The identity of fragments SEQ ID No. 15 to SEQ ID No. 18 will advantageously be confirmed by sequencing.

The marker can be any marker known to those skilled in the art, but is preferably digoxigenin (DIG).

The use of the probes described above to demonstrate the product of the amplification reaction SEQ ID No. 8 is particularly advantageous since it enables the bovine origin of this amplification product to be confirmed and therefore also enables the specificity and sensitivity of the process to be improved.

The present invention also relates to complementary and inverse/complementary oligonucleotides to the oligonucleotides described above.

Those skilled in the art could advantageously refer to the general manual of SAMBROOK et al. 1989, Molecular Cloning: A Laboratory Manual, Cold Spring Harbor Laboratory, Cold Spring Harbor, N.Y., or to one of its recent re-issues, for carrying out the molecular biology techniques of the present invention.

The present invention enables the presence of compounds of bovine origin to be detected in products used in agricultural food production and in the cosmetics industry, such as cooked or raw meats, pellets and meals used for feeding cattle, composts, manures and dungs, products based on blood, bone meal, hide or guano, gelatines and animal fats.

The present invention is illustrated by the examples which follow, but without being limited by them.

EXAMPLE 1

Extraction and Analysis of the DNA of Various Types of Organic Matter.

In order to be able to develop a method for detection, by gene amplification, of compound of bovine origin in products used in agricultural food production and in the cosmetics industry, the experiments described in this first example were carried out with to various types of samples representing potential sources of the spread of BSE.

The samples selected are divided into 12 groups of finished products, or products included in the composition of finished products:

| | | |
|---|---|---|
| Soil improvers, composts | Manures | Guano |
| Dungs, droppings | Moulds | Pellets for cattle |
| Meals for cattle | Hides | Bone and bone meal |
| Feathers | Blood | Gelatines, fat. |

To be able to carry out an analysis of any sample by PCR, it is necessary to have available DNA extraction techniques. Given the diversity of the samples tested, several techniques are used:

1) Extraction of the DNA by the Phenol/Chloroform Method.

This method is preferably applied to samples in which the content of components of animal origin is predominant (meals, pellets, bone, blood, feathers, hides . . . ).

This method uses a technique described by HÄNNI et al., 1990, C. R. Acad. Sci. Paris., 310, 365–370 and by HÄNNI et al., 1995, Nucl. Acids Res., 23, 881–882 describing the extraction of DNA from bone and teeth.

0.5 g powder is incubated for three hours at 56° C. in 2.5 ml lysis buffer of the following composition:

Tris 100 mM, pH 8

NaCl 100 mM sodium sarcosinate 1%.

Containing: 200 µg/ml proteinase K, enabling the proteins to be degraded and the nucleic acids to be liberated.

The lysate is then extracted by one volume of phenol/chloroform 1/1 to remove the protein part of the lysate. A second extraction is carried out. The aqueous phase is then extracted by 1 volume of chloroform.

The DNA is then precipitated by 0.6 volume of isopropanol and 0.1 volume of ammonium acetate 2 M at −20° C. for at least 2 hours. It is subsequently collected by centrifugation (15 min at 12,000 rpm) and then washed with ethanol at 70° C. (kept at −20° C.). After evaporation of the residual alcohol (1 to 2 hours in a fume cupboard), the DNA is dissolved in water for injection (water FI; the volume of water depends on the amount of DNA collected).

2) Extraction by the CTAB (Cetyltrimethylammonium Bromide) Method.

This method, described by MURRAY (Nucleic Acid Res. 8 (19), 4321–4325 (1980)), is preferably applied to samples containing fragments of vegetable origin mixed with products of animal origin (dungs, composts, soil improvers, manures, mould).

1 g of sample is incubated for 3 hours at 56° C. in 2.5 ml of lysis buffer, the composition of which is:

Tris 10 mM pH 8

EDTA 0.1 mM sodium dodecylsulphate 1% proteinase K 100 mug/ml

450 µl NaCl 5 M and 375 µl CTAB 10% NaCl 0.7 M, preheated to 65° C., are added and the entire mixture is incubated for 20 min at 65° C. One volume of chloroform is then added. After stirring and centrifugation (10 min at 12,000 rpm at 4° C.), the aqueous phase is collected and re-extracted a second time to clarify it. It is extracted again by one volume of phenol/chloroform. The procedure following the extraction is as indicated in paragraph 1.

3) Quantitative Analysis of the DNA Extracted.

The analysis method used is that of LABARCA (1980 Analytical Biochemistry 102, 344–352). It is based on the reaction of intercalation of a molecule, Hoechst 33258 (2-(2-4 hydroxyphenyl)benzydalozyl)-6(1-methyl-4-piperazyl)-benzymidazol, 3HCl) into the double helix of the DNA to be analysed. When irradiated at 356 nm, the complex of Hoechst 33258/DNA emits a characteristic fluorescence signal (458 nm).

The emission of the fluorescence is proportional to the amount of DNA in solution; the result is read by means of a fluorimeter (DyNA quant-Hoeffer). The DNA of the sample to be analysed is added to 2 ml Tris buffer 10 mM, pH 7.4, EDTA 1 mM, NaCl 0.2 M containing 1 µg 33258/ml.

By calibration of the apparatus with the aid of a standard DNA solution of known concentration, the amount of DNA extracted from the sample is measured.

Table 1 which follows shows that the techniques described enable the DNA to be demonstrated in all the samples in an amount sufficient for analysis by the PCR method according to the present invention.

EXAMPLE 2

Amplification by PCR of Sequences of Bovine mtDNA from DNA Extracted from Samples.

1) Purification of the Extracted DNA on Silica.

To be able to carry out the PCR reaction under optimum reaction conditions, it is necessary to purify the extracted DNA beforehand. The purification described below uses a technique described by BOOM et al. (1990, J. Clin. Microbiol. 28, 495–503).

50 µl crude DNA obtained by one or other of the methods described in example 1 are diluted in 400 µl of a buffer obtained by addition of 120 g guanidinium thiocyanate, 22 ml EDTA 0.2 M, pH 8, and 2.6 ml Triton X100 to 100 ml of a Tris buffer 0.1 mM, pH 6.4.

This solution is incubated for 5 min at room temperature with 300 µl silica (Wizard DNA clean up System Promega ref A7280: silica and minicolumns). The silica is washed on a column with 2 ml 80% isopropanol. The column is centrifuged for 2 min at 12,000 rpm to remove the residual alcohol, and 50 µl water FI, preheated to 70° C., are added to elute the DNA bonded to the silica (incubation for 5 to 30 min at 70° C.).

The eluate containing the DNA collected by centrifugation (12,000 rpm, 2 min) is ready to be used for the PCR.

If necessary, a second purification on silica is carried out.

2) The PCR Reaction

The PCR was carried out with the two oligonucleotide primers SEQ ID No. 3 and SEQ ID No. 6 showing the sequences SEQ ID No. 3 and SEQ ID No. 6 respectively.

The amplifications were carried out in a total volume of 50 µl containing:

5 µl of a buffer Taqx10 (free from Mg++) commercially obtainable with the enzyme 5 µl of a mixture of dATP, dCTP, dGTP and dTTP (2 mM each)

3 µl MgCl$_2$ 25 mM 0.5 µl albumin 20 mg/ml

5 µl of each of the primers SEQ ID No. 3 and SEQ ID No. 6 (10 µM each)

10 µl DNA of the genome matrix (from 100 ng to 1 µg)

0.2 µl Taq DNA polymerase (5 units/µl)

16.3 µl sterile distilled water

With the exception of the genome matrix, the primers and the Taq DNA polymerase, all the above substances make up the base buffer solution prepared in bulk and stored at −20° C.

All the amplifications were carried out with a "Perkin-Elmer" thermal cycle control apparatus with the following temperature programme:

| "PCR programme" | |
|---|---|
| 1 initial cycle comprising | 5 min at 94° C. |
| 9 cycles comprising | 30 s at 94° C. |
| | 30 s at 55° C. (and then a temperature reduced by |
| | 0.5° C. each cycle to 51° C.) |
| | 30 s at 72° C. |
| 32 cycles comprising | 30 s at 94° C. |
| | 30 s at 51° C. |
| | 30 s at 72° C. |
| 1 final cycle comprising | 7 min at 72° C. |
| | a few minutes to several hours at 4° C. |

The amplification products are analysed by electrophoresis on agarose gel at 1.5% under a constant voltage, of 130 V for 45 min and with the aid of ethidium bromide for visualization of the amplification products obtained.

Figure 1:
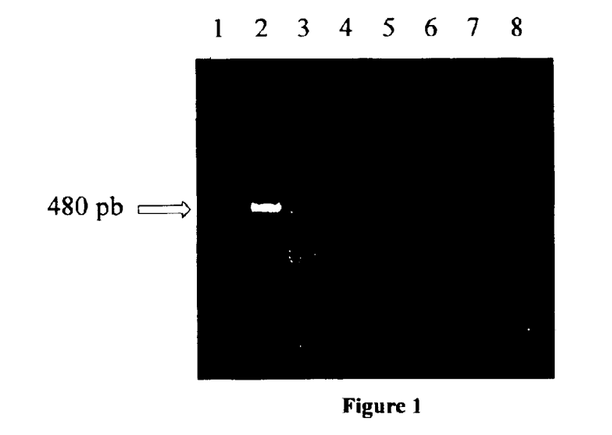
FIG. 1 shows an agarose gel stained with ethidium bromide. The DNAs of beef, horse, sheep, pig, duck, chicken and turkey (wells 2 to 8 respectively) have been amplified with the aid of the primers SEQ ID No. 6 (PBF9) and SEQ ID No. 3 (PBR6). Well 1 corresponds to a negative control. The amplification product migrates, forming a band of 480 base pairs.

The PCR reaction using the pair of primers SEQ ID No. 3 and SEQ ID No. 6 was carried out on a series of DNA extracts obtained from various animal and plant tissues. A single amplification product was found (fragment having a length of 480 base pairs—480 bp) for the bovine tissues, and no product was found for any of the other DNAs tested (FIG. 1). The primers SEQ ID No. 3 and SEQ ID No. 6 are therefore suitable for identification of specific bovine DNA in a PCR application.

Figure 2:
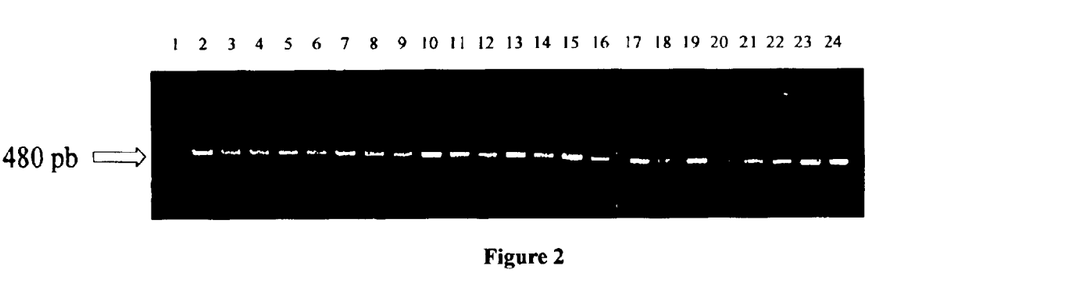
FIG. 2 is another agarose gel on which the amplification products of the DNA of various European bovine breeds have been migrated: bleu-blanc-belge (wells 2 and 3), Limousine (wells 4 and 5), Charolaise (wells 6 to 10), Normande (wells 11 and 12), Prim'Holstein (wells 13 to 16), Blonde d'Aquitaine (wells 17 to 20), Frisonne (well 21), Croisée (wells 22 and 23) and Parthenaise (well 24). Well 1 corresponds to a negative control.

In addition to these results, the PCR technique using these two primers was applied to the DNA extracted from animal tissues of various European bovine breeds (Blanc-Bleu Belge, Limousine, Charolaise, Normande, Prim'Holstein, Charolaise crossed Normande, Blonde Aquitaine, Parthenaise). All the samples gave the same profile (a single fragment of 480 bp), indicating that, the method can be applied whatever the origin of the bovine DNA analysed (FIG. 2).

EXAMPLE 3

Characterization of the DNA Amplified in the PCR Reaction by the So-Called "Southern" Technique.

Confirmation of the "bovine" character of the PCR amplification product (480 bp) is obtained by hybridization of an oligonucleotide probe corresponding to the identification sequence BH1 (SEQ ID No. 7) with this product. The BH1 probe used for this purpose is marked with digoxigenin (DIG) by means of a commercial kit ("Dig oligonucleotide 3'-end labelling kit—Boehringer).

After capillary transfer on to a nylon membrane, the amplification products are denatured before covalent bonding to the membrane by UV. After incubation of the membrane in a hybridization buffer containing the marked BH1 probe, washings are carried out and the probe is then visualized by a system of anti-DIG antibodies coupled to alkaline phosphatase in the presence of nitroblue tetrwzolium chloride and 5-bromochloro-3-indolyl phosphate. The amplification products are thus characterized in this reaction by the appearance of a brown-violet coloration.

Figure 3:
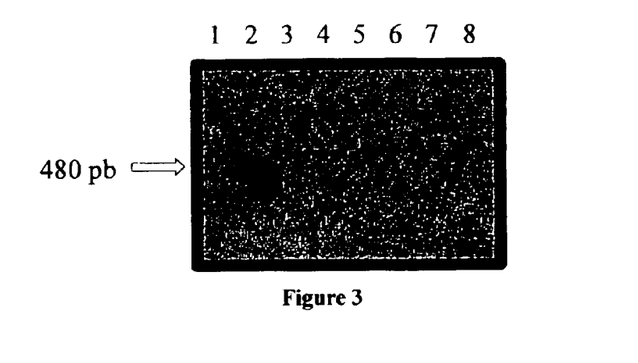
FIG. 3 shows the transfer by the southern technique of an agarose gel of FIG. 1 hybridized with the aid of the marked probe SEQ ID No. 7 (BH1).

By using the analysis by hybridization/transfer of the "southern" type, it is found that the BH1 probe hybridizes specifically with the sequence of bovine mtDNA amplified by means of the primers SEQ ID No. 3 and SEQ ID No. 6, and not with the DNA of other animal and plant species (FIG. 3).

EXAMPLE 4

Use of PCR and "Southern" Techniques for Detection of Animal Meals of Bovine Origin in Cattle Feeds.

The processes of examples 1, 2 and 3 were applied to samples of cattle feeds (in the form of meals or pellets) containing no products of bovine origin and to those in which meal of bovine by-products had been incorporated experimentally in amounts varying from 5 to 0.01%.

A specific signal which is proportional to the level of incorporation was obtained by PCR amplification using the primers SEQ ID No. 3 and SEQ ID No. 6 on all the samples containing at least 0.1% of meal of bovine origin.

Figure 4:
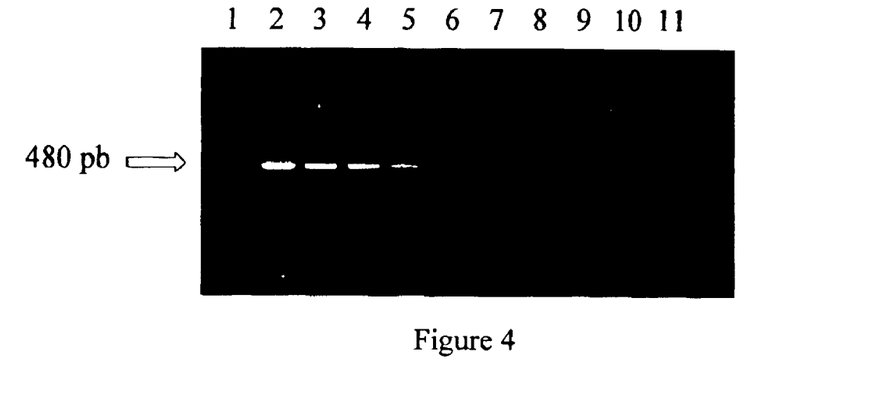
FIG. 4 is an agarose gel with the amplification products of foods for cattle having levels of incorporation of bovine meal of, respectively, 5; 2.5; 1; 0.5; 0.25; 0.1; 0.075; 0.06; 0.05; 0.01% (wells 2 to 11 respectively). Well 1 corresponds to a negative control.
Figure 5:
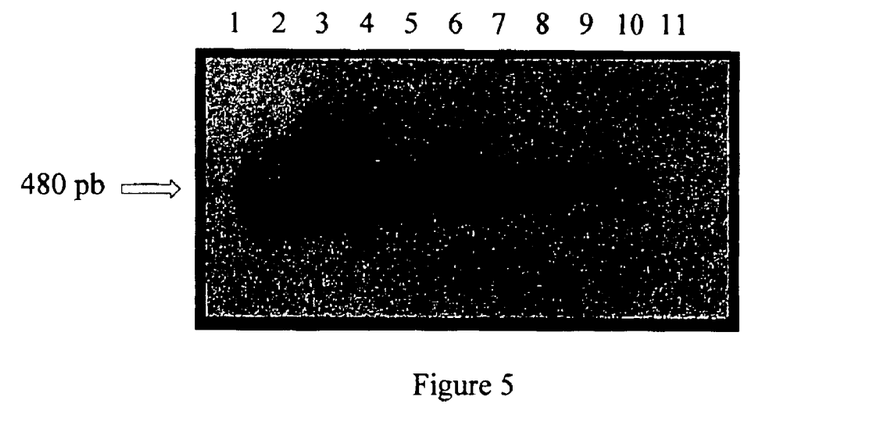
FIG. 5 is a transfer by the southern method of the gel shown on FIG. 4 hybridized by the marked probe SEQ ID No. 7 (BH1).

Application of the "southern" technique with the oligonucleotide probe BH1 to the amplification products obtained above enables samples containing meat meal to be detected specifically, this time with a detection limit reduced to 0.05% (FIG. 4).

EXAMPLE 5

Use of PCR and "Southern" Techniques for Detection of Products of Bovine Origin in All Samples.

The processes of examples 1, 2 and 3 were applied to various samples which may contain varying levels of products of bovine origin, such as cooked or raw meats, pellets and meals used for feeding cattle, composts, manures and dungs, products based on blood, bone meal, hide or guano, gelatines and animal fats.

A specific signal was obtained with all the samples tested which contained products of bovine origin (table 2 below). Perfect correlation between the recognized presence of product of bovine origin in the samples and the PCR signal is found (presence of the amplification product of 480 bp which hybridizes with the marked BH1 probe).

TABLE 1

Analysis by H33258 of the DNA extracted from samples
Results expressed in μg DNA extracted from 0.5 g of product

| Category of product | Phenol/chloroform extraction | CTAB extraction |
|---|---|---|
| 1 Food* | 105.5 | 228.4 |
| 2 Food | 42.5 | 345.2 |
| 3 Food | 34.2 | 53.4 |
| 4 Compost | 3.6 | 287.4 |
| 5 Compost | 6.4 | 47.19 |
| 6 Hide | 0.4 | 0.6 |
| 7 Hide | 0.12 | 0.8 |
| 8 Manure | 10.2 | 57.6 |
| 9 Manure | 0.95 | 3.05 |
| 10 Manure | 0.5 | 1.2 |
| 11 Meal | 291.4 | 346.2 |
| 12 Meal | 439.6 | 309.2 |
| 13 Meal | 322 | 278 |
| 14 Meal | 502.3 | 468.95 |
| 15 Meal | 198.6 | 154 |
| 16 Meal | 202 | 189.2 |
| 17 Droppings | 86.9 | 86.94 |
| 18 Dung | 0.9 | 8.78 |
| 19 Dung | 1.1 | 14.6 |
| 20 Dung | 2.3 | 10.1 |
| 21 Dung | 4.6 | 24.09 |
| 22 Fat | 0.01 | 0.01 |
| 23 Gelatine | 0.01 | 0.01 |
| 24 Guano | 3.9 | 334.2 |
| 25 Bone | 35.7 | 149.7 |
| 26 Bone | 12.1 | 2.4 |
| 27 Bone | 114.6 | 6.7 |
| 28 Feathers | 106.7 | 333.8 |
| 29 Feathers | 128.2 | 257.4 |
| 30 Blood | 1074.5 | 1147.8 |
| 31 Blood | 7.47 | 10.7 |
| 31 Mould | 0.65 | 2.3 |
| 30 Mould | 5.42 | 18.79 |

*Pelletted food for cattle

TABLE 2

Detection of products of bovine origin by the PCR method using the primers PBF9 and PBR6

| Nature of the sample analysed by PCR | Known presence (P) or absence (A) of by-products of bovine origin in the sample analysed | PCR reaction +: presence of amplification product of 480 bp; −: absence of amplification product |
|---|---|---|
| 1 Food* | P | + |
| 2 Food | P | + |
| 3 Food | P | + |
| 4 Compost | A | − |
| 5 Compost | P | + |
| 6 Hide | P | + |
| 7 Hide | P | + |
| 8 Manure | P | + |
| 9 Manure | A | − |
| 10 Manure | A | − |
| 11 Meal | A | − |
| 12 Meal | P | + |
| 13 Meal | P | + |
| 14 Meal | P | + |
| 15 Meal | P | + |
| 16 Meal | P | + |
| 17 Droppings | A | − |
| 18 Dung | P | + |
| 19 Dung | A | − |
| 20 Dung | P | + |
| 21 Dung | P | + |
| 22 Fat | P | + |
| 23 Gelatine | P | + |
| 24 Guano | A | − |
| 25 Bone | P | + |
| 26 Bone | P | + |
| 27 Bone | P | + |
| 28 Feathers | A | − |
| 29 Feathers | A | − |
| 30 Blood | P | + |
| 31 Blood | P | + |
| 31 Mould | P | + |
| 30 Mould | A | − |

*Pelletted food for cattle

What is claimed is:

1. Pairs of oligonucleotide primers, each primer pair being selected from the group of primer pairs consisting of: SEQ ID NO: 9 with SEQ ID NO: 10; SEQ ID NO: 6 with SEQ ID NO: 11; SEQ ID NO: 12 with SEQ ID NO: 3; and SEQ ID NO: 13 with SEQ ID NO: 14.

2. Pairs of primers consisting of one of SEQ ID NO: 1 and SEQ ID NO: 3 ; and one of SEQ ID NO: 4 and SEQ ID NO: 6.

* * * * *

SEQUENCE LISTING

```
<160> NUMBER OF SEQ ID NOS: 19

<210> SEQ ID NO 1
<211> LENGTH: 43
<212> TYPE: DNA
<213> ORGANISM: Artificial Sequence
<220> FEATURE:
<223> OTHER INFORMATION: Description of Artificial Sequence:
      oligonucleotide used for detecting the presence of
      biological matters of Bovine origin

<400> SEQUENCE: 1
taatgtccat gcttatcatt atgctggtgc tcaagatgca gtt          43

<210> SEQ ID NO 2
<211> LENGTH: 15
<212> TYPE: DNA
<213> ORGANISM: Artificial Sequence
<220> FEATURE:
<223> OTHER INFORMATION: Description of Artificial Sequence:
      oligonucleotide used for detecting the presence of
      biological matters of Bovine origin

<400> SEQUENCE: 2
ytatcattat gctgg                                          15

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence:
      oligonucleotide used for detecting the presence of
      biological matters of Bovine origin
```

```
<400> SEQUENCE: 3
catgcytatc attatgctgg                                              20

<210> SEQ ID NO 4
<211> LENGTH: 46
<212> TYPE: DNA
<213> ORGANISM: Artificial Sequence
<220> FEATURE:
<223> OTHER INFORMATION: Description of Artificial Sequence:
      oligonucleotide used for detecting the presence of
      biological matters of Bovine origin

<400> SEQUENCE: 4
attatatgcc ccatgcatat aagcaagtac atgacctcta tagcag                 46

<210> SEQ ID NO 5
<211> LENGTH: 15
<212> TYPE: DNA
<213> ORGANISM: Artificial Sequence
<220> FEATURE:
<223> OTHER INFORMATION: Description of Artificial Sequence:
      oligonucleotide used for detecting the presence of
      biological matters of Bovine origin

<400> SEQUENCE: 5
taagcaagta catga                                                   15

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence:
      oligonucleotide used for detecting the presence of
      biological matters of Bovine origin

<400> SEQUENCE: 6
gcatataagc aagtacatga                                              20

<210> SEQ ID NO 7
<211> LENGTH: 27
<212> TYPE: DNA
<213> ORGANISM: Artificial Sequence
<220> FEATURE:
<223> OTHER INFORMATION: Description of Artificial Sequence:
      oligonucleotide used for detecting the presence of
      biological matters of Bovine origin

<400> SEQUENCE: 7
cttgatagta tatctattat atattcc                                      27

<210> SEQ ID NO 8
<211> LENGTH: 482
<212> TYPE: DNA
<213> ORGANISM: Artificial Sequence
<220> FEATURE:
<223> OTHER INFORMATION: Description of Artificial Sequence:
      oligonucleotide used for detecting the presence of
      biological matters of Bovine origin
<223> OTHER INFORMATION: "n" at various positions throughout the
      sequence represents a, t, c or g

<400> SEQUENCE: 8
gcatataagc aagyacatra yyyctayavy agtacataay rcatayaatt attrayygta   60
catagtacat tatrtcaaay ycatyctyra yaryatatyt ayyatatayy ycytnccayt  120
```

```
agatcacgag cttaaytacc atgccgcgtg aaaccarcaa cccgctrrgc agnggatccc    180
tcttctcgct ccgggcccat arayygtggg ggtcgctaty yartgaaytt taycaggcat    240
ctggttcttt cttcagggcc atctcatcta aaryrgtcca ttcyttcctc ttaaataaga    300
catctcgatg gactaatgrc taatcagccc atgctcacac ataactgtgy tgtcatacat    360
ttggtatttt tttattttgg gggatgcttg gactcagcta tggccgtcaa aggccctgac    420
ccggagcatc tattgtagct ggacttaact gcatcttgag caccagcata atgatargcr    480
tg                                                                   482
```

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence:
oligonucleotide used for detecting the presence of
biological matters of Bovine origin

<400> SEQUENCE: 9

```
gagccttatc agtattaaat ttatc                                          25
```

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence:
oligonucleotide used for detecting the presence of
biological matters of Bovine origin

<400> SEQUENCE: 10

```
cattaatgtt atgtacatta                                                20
```

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence:
oligonucleotide used for detecting the presence of
biological matters of Bovine origin

<400> SEQUENCE: 11

```
tttcacgcgg catggtaatt                                                20
```

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence:
oligonucleotide used for detecting the presence of
biological matters of Bovine origin

<400> SEQUENCE: 12

```
atccaatgaa ttttaccagg                                                20
```

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence:
oligonucleotide used for detecting the presence of
biological matters of Bovine origin

<400> SEQUENCE: 13
gtcaatggtc acaggacata                                              20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence:
      oligonucleotide used for detecting the presence of
      biological matters of Bovine origin

<400> SEQUENCE: 14
attgactttg tttggagtgc                                              20

<210> SEQ ID NO 15
<211> LENGTH: 159
<212> TYPE: DNA
<213> ORGANISM: Artificial Sequence
<220> FEATURE:
<223> OTHER INFORMATION: Description of Artificial Sequence:
      oligonucleotide used for detecting the presence of
      biological matters of Bovine origin

<400> SEQUENCE: 15
gagccttatc agtattaaat ttatcaaaaa tcccaataac tcaacacaga atttgcaccc    60
taaccaaata ttacaaacac cactagctaa cataacacgc ccatacacag accacagaat   120
gaattaccta cgcaagcggt aatgtacata acattaatg                          159

<210> SEQ ID NO 16
<211> LENGTH: 153
<212> TYPE: DNA
<213> ORGANISM: Artificial Sequence
<220> FEATURE:
<223> OTHER INFORMATION: Description of Artificial Sequence:
      oligonucleotide used for detecting the presence of
      biological matters of Bovine origin

<400> SEQUENCE: 16
gcatataagc aagtacatga cctctatagc agtacataat acatataatt attgactgta    60
catagtacat tatgtcaaat tcattcttga tagtatatct attatatatt ccttaccatt   120
agatcacgag cttaattacc atgccgcgtg aaa                                153

<210> SEQ ID NO 17
<211> LENGTH: 265
<212> TYPE: DNA
<213> ORGANISM: Artificial Sequence
<220> FEATURE:
<223> OTHER INFORMATION: Description of Artificial Sequence:
      oligonucleotide used for detecting the presence of
      biological matters of Bovine origin

<400> SEQUENCE: 17
atccaatgaa ttttaccagg catctggttc tttcttcagg gccatctcat ctaaaacggt    60
ccattctttc ctcttaaata agacatctcg atggactaat ggctaatcag cccatgctca   120
cacataactg tgctgtcata catttggtat tttttattt tggggatgc ttggactcag    180 ctatggccgt caaaggccct gacccggagc atcattgta gctggactta actgcatctt   240
gagcaccagc ataatgataa gcatg                                        265

<210> SEQ ID NO 18

```
<211> LENGTH: 158
<212> TYPE: DNA
<213> ORGANISM: Artificial Sequence
<220> FEATURE:
<223> OTHER INFORMATION: Description of Artificial Sequence:
      oligonucleotide used for detecting the presence of
      biological matters of Bovine origin

<400> SEQUENCE: 18
gtcaatggtc acaggacata aattatatta tatatccccc cttcataaaa attccccct      60 taaatatcta ccaccacttt taacagactt ttccctagat acttatttaa atttttcacg   120
ctttcaatac tcaatttagc actccaaaca aagtcaat                            158

<210> SEQ ID NO 19
<211> LENGTH: 25
<212> TYPE: DNA
<213> ORGANISM: Artificial Sequence
<220> FEATURE:
<223> OTHER INFORMATION: Description of Artificial Sequence:
      oligonucleotide used for detecting the presence of
      biological matters of Bovine origin

<400> SEQUENCE: 19
taarccgtgg gggtcgctat ccaat                                           25
```